(12) United States Patent
Lim et al.

(10) Patent No.: US 6,774,244 B2
(45) Date of Patent: Aug. 10, 2004

(54) PRIMARY INTERMEDIATES FOR OXIDATIVE COLORATION OF HAIR

(75) Inventors: Mu-Ill Lim, Trumbull, CT (US); Yuh-Guo Pan, Stamford, CT (US)

(73) Assignee: The Procter & Gamble Company, Cincinnati, OH (US)

( * ) Notice: Subject to any disclaimer, the term of this patent is extended or adjusted under 35 U.S.C. 154(b) by 146 days.

(21) Appl. No.: 10/052,317

(22) Filed: Jan. 18, 2002

(65) Prior Publication Data

US 2002/0170124 A1 Nov. 21, 2002

Related U.S. Application Data

(60) Provisional application No. 60/263,460, filed on Jan. 23, 2001.

(51) Int. Cl.[7] .................. C07D 207/00; C07D 333/20; C07C 211/45
(52) U.S. Cl. .................. 548/575; 549/75; 564/336
(58) Field of Search .................. 546/223; 548/372.5, 548/559, 575; 549/21, 38, 68, 369, 377, 480, 510, 75; 564/336

(56) References Cited

FOREIGN PATENT DOCUMENTS

DE    196 04 178 A1    2/1996    ............ A61K/7/13

*Primary Examiner*—John R. Hardee
(74) *Attorney, Agent, or Firm*—Brian M. Bolam; Marianne Dressman; Tara M. Rosnell

(57) ABSTRACT

Primary intermediates for hair coloring compositions for oxidative dyeing of hair are compounds of the formula (1):

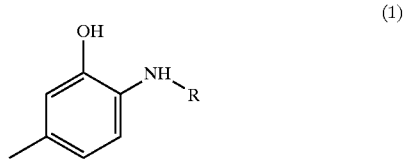

(1)

wherein R is selected from $C_1$ to $C_5$ alkyl or hydroxyalkyl, a $C_3$ to $C_6$ cyclic ring containing hetero atoms selected from O, S and N atoms, and —$CH_2$—Ar where Ar is an aromatic ring wherein the aromatic ring may be substituted with one or two hydroxy $C_1$ to $C_3$ alkoxy, or amino groups.

5 Claims, No Drawings

PRIMARY INTERMEDIATES FOR OXIDATIVE COLORATION OF HAIR

This application claims the benefit of Provisional Application No. 60/263,460, filed Jan. 23, 2001.

FIELD OF THE INVENTION

This invention relates to new 2-substituted-amino-5-methyl-phenol compounds and compositions containing these compounds as primary intermediates for oxidative coloring of hair fibers.

BACKGROUND TO THE INVENTION

Coloration of hair is a procedure practiced from antiquity employing a variety of means. In modern times, the method most extensively to color hair is an oxidative dyeing process utilizing one or more oxidative hair coloring agents in combination with one or more oxidizing agents.

Most commonly a peroxy oxidizing agent is used in combination with one or more oxidative hair coloring agents, generally small molecules capable of diffusing into hair and comprising one or more primary intermediates and one or more couplers. In this procedure, a peroxide material, such as hydrogen peroxide, is employed to activate the small molecules of primary intermediates so that they react with couplers to form larger sized compounds in the hair shaft to color the hair in a variety of shades and colors.

A wide variety of primary intermediates and couplers have been employed in such oxidative hair coloring systems and compositions. Among the primary intermediates employed there may be mentioned p-phenylenediamine, p-toluenediamine, p-aminophenol, 4-amino-3-methylphenol, N,N-bis(2-hydroxyethyl)-p-phenylene diamine, 1-(2-hydroxyethyl)-4,5-diaminopyrazole and as couplers there may be mentioned resorcinol, 2-methylresorcinol, 3-aminophenol, 2,4-diaminophenoxyethanol, and 5-amino-2-methylphenol.

There are numerous additional requirements for oxidation dye compounds that are used to dye human hair besides the color or the desired intensity. Thus, the dye compounds must be unobjectionable in regard to toxicological and dermatological properties and must provide the desired hair color with a good light fastness, good selectivity, fastness to a permanent wave treatment, acid fastness and fastness to rubbing. The color of the hair dyed with the dye compounds in each case must be stable for at least 4 to 6 weeks to light, rubbing and chemical agents. Furthermore, an additional requirement is the production of a broad palette of different color shades using different developer and coupler substances.

For providing a yellow or orange yellow coloration to hair, resorcinol and 2-methyl resorcinol have been extensively used in combination with p-aminophenol. Coupling of p-aminophenol with 2-methyl resorcinol provides weak orange yellow, while coupling of p-aminophenol with resorcinol gives weak yellow green. 6-Amino-m-cresol (U.S. Pat. No. 4,396,392) as well as direct dye 2-amino-4-nitro-6-chlorophenol is also used in current practices. A combination of tetraaminopyrimidine and 3,4-dimethyl-2,6-dihydroxy pyridine (EP 63736 A2) or a combination of 6-hydroxyindole and p-aminophenol (U.S. Pat. No. 5,279,620) are also used. 6-Hydroxyindole couples with p-aminophenol and p-phenylenediamine to provide golden beige and medium golden brown, respectively. However, these yellow couplers suffer from weak and dull coloration, especially in the presence of primary intermediates and couplers. Therefore, there is a need to develop more compounds for providing reliable yellow and orange yellow coloration in oxidative hair coloring.

SUMMARY OF THE INVENTION

It is therefore an object of this invention to provide new primary intermediate compounds useful for providing yellow or orange yellow color shades with various combinations of primary intermediates and couplers.

It has been discovered that new 2-substituted-amino-5-methyl-phenol compounds are suitable primary intermediates for hair coloring compositions and systems for providing good oxidative coloration of hair and for providing acceptable light fastness, good selectivity, fastness to shampooing, fastness to permanent wave treatment, and suitable for providing a wide variety of different color shades with various primary intermediate and coupler compounds.

The invention provides new 2-substituted-amino-5-methyl-phenol compounds of Formula (1):

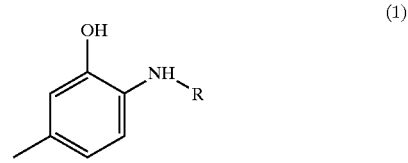

(1)

wherein R is selected from $C_1$ to $C_5$ alkyl or hydroxyalkyl, a $C_3$ to $C_6$ cyclic ring containing hetero atoms selected from O, S and N atoms, and —$CH_2$—Ar where Ar is an aromatic ring wherein the aromatic ring may be substituted with one or two hydroxy, $C_1$ to $C_3$ alkoxy, or amino groups.

These novel primary intermediates are used to provide coloration to hair in which there is good dye uptake by the hair and provides shades or colors that are stable over a relatively long period of time. The novel primary intermediates provide for dyeing of hair to impart color or shades that possess good wash fastness, good selectivity, and do not undergo significant changes on exposure to light, perspiration or shampooing.

DETAILED DESCRIPTION OF THE INVENTION

The 2-substituted-amino-5-methyl-phenol compounds of this invention are those of formula (1)

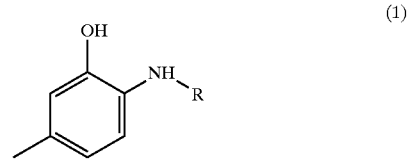

(1)

wherein R is selected from $C_1$ to $C_5$ alkyl or hydroxyalkyl, a $C_3$ to $C_6$ cyclic ring containing hetero atoms selected from O, S and N atoms, and —$CH_2$—Ar where Ar is an aromatic ring wherein the aromatic ring may be substituted with one or two hydroxy, $C_1$ to $C_3$ alkoxy, or amino groups.

Preferably, R is $C_1$ to $C_3$ alkyl, benzyl, thiophen-ylmethyl and pyrrolylmethyl.

The new 2-substituted-amino-5-methyl-phenol compounds of formula (1) of this invention can be prepared according to the following reaction sequence wherein R is as defined herein before.

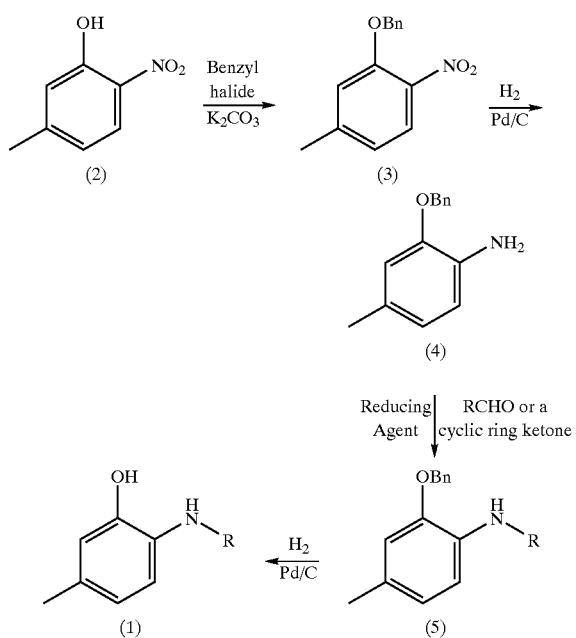

In this synthesis the new 2-substituted amino-5-methyl-phenol compounds of formula (1) of this invention can be prepared by reaction of 5-methyl-2-nitro-phenol of formula (2) with a benzyl halide, such as benzyl bromide, in the presence of potassium carbonate in dimethylformamide (DMF) to produce the compound of formula (3), and catalytically hydrogenating the compound of formula (3) with Pd/C at about 60 psi hydrogen to provide a compound of formula (4) which is reductively aminated with a compound of the formula RCHO or a $C_3$ to $C_6$ cyclic ring ketone and reducing agents, such as LiAlH$_4$, DIBAL-H, NaBH$_4$, sodium triacetoxyborohydride, zinc borohydride, sodium cyanoborohydride, zinc acetate and polymethylhydrosiloxane (PMHS/Ti(O$^1$Pr)$_4$ to produce a compound of formula (5) and catalytically hydrogenating the compound of formula (5) to provide a compound of formula (1).

SYNTHESIS EXAMPLES 1 to 4

Employing the appropriate reagent of the formula RCHO in the this reaction procedure, the following compounds of formula (1) can be prepared:

2-benzylamino-5-methyl-phenol;
5-methyl-2-[1-H-pyrrol-2-ylmethyl)-amino]-phenol;
2-isopropylamino-5-methyl-phenol; and
5-methyl-2-[(thiophen-2-ylmethyl)-amino]-phenol.

As used herein, the term "hair dyeing composition" (also synonymously referred to herein as the hair dye composition, the hair coloring composition, or the hair dye lotion) refers to the composition containing oxidation dyes, including the novel compounds described herein, prior to admixture with the developer composition. The term "developer composition" (also referred to as the oxidizing agent composition or the peroxide composition) refers to compositions containing an oxidizing agent prior to admixture with the hair dyeing composition. The term "hair dye product" or "hair dye system"(also referred to as the hair dyeing system, hair dyeing product, or hair coloring system) interchangeably refer to the combination of the hair dyeing composition and the developer composition before admixture, and may further include a conditioner product and instructions, such product or system often being provided packaged as a kit. The term "hair dyeing product composition" refers to the composition formed by mixing the hair dyeing composition and the developer composition. "Carrier" (or vehicle or base) refers to the combination of ingredients contained in a composition excluding the active agents (e.g., the oxidation hair dyes of the hair dyeing composition).

Hair coloring (i.e., hair dyeing) compositions of this invention can contain, in combination with oxidation dye couplers, a novel primary intermediate of this invention as the sole primary intermediate or can also contain other primary intermediates. Thus, one or more suitable primary intermediates may be used in combination with the novel primary intermediates of this invention.

Suitable known primary intermediates include, for example, p-phenylenediamine derivatives such as: benzene-1,4-diamine (commonly known as p-phenylenediamine), 2-methyl-benzene-1,4-diamine, 2-chloro-benzene-1,4-diamine, N-phenyl-benzene-1,4-diamine, N-(2-ethoxyethyl)benzene-1,4-diamine, 2-[(4-amino-phenyl)-(2-hydroxy-ethyl )-amino]-ethanol, (commonly known as N,N-bis(2-hydroxyethyl)-p-phenylenediamine) (2,5-diamino-phenyl)-methanol, 1-(2,5-diamino-phenyl)-ethanol, 2-(2,5-diamino-phenyl)-ethanol, N-(4-aminophenyl)benzene-1,4-diamine, 2,6-dimethyl-benzene-1,4-diamine, 2-isopropyl-benzene-1,4-diamine, 1-[(4-aminophenyl)amino]-propan-2-ol, 2-propyl-benzene-1,4-diamine, 1,3-bis[(4-aminophenyl)(2-hydroxyethyl)amino] propan-2-ol, $N^4,N^4$,2-trimethylbenzene-1,4-diamine, 2-methoxy-benzene-1,4-diamine, 1-(2,5-diaminophenyl)ethane-1,2-diol, 2,3-dimethyl-benzene-1,4-diamine, N-(4-amino-3-hydroxy-phenyl)-acetamide, 2,6-diethylbenzene-1,4-diamine, 2,5-dimethylbenzene-1,4-diamine, 2-thien-2-ylbenzene-1,4-diamine, 2-thien-3-ylbenzene-1,4-diamine, 2-pyridin-3-ylbenzene-1,4-diamine, 1,1'-biphenyl-2,5-diamine, 2-(methoxymethyl)benzene-1,4-diamine, 2-(aminomethyl)benzene-1,4-diamine, 2-(2,5-diaminophenoxy)ethanol, N-[2-(2,5-diaminophenoxy) ethyl]-acetamide, N,N-dimethylbenzene-1,4-diamine, N,N-diethylbenzene-1,4-diamine, N,N-dipropylbenzene-1,4-diamine, 2-[(4-aminophenyl) (ethyl)amino]ethanol, 2-[(4-amino-3methyl-phenyl)-(2-hydroxy-ethyl)-amino]-ethanol, N-(2-methoxyethyl)-benzene-1,4-diamine, 3-[(4-aminophenyl)amino]propan-1-ol, 3-[(4-aminophenyl)-amino]propane-1,2-diol, N-{4-[(4-aminophenyl) amino]butyl}benzene-1,4-diamine, and 2-[2-(2-{2-[(2, 5-diaminophenyl)-oxy]ethoxy}ethoxy)ethoxy] benzene-1,4-diamine;

p-aminophenol derivatives such as: 4-amino-phenol (commonly known as p-aminophenol), 4-methylamino-phenol, 4-amino-3-methyl-phenol, 4-amino-2-hydroxymethyl-phenol), 4-amino-2-methyl-phenol, 4-amino-2-[(2-hydroxy-ethylamino)-methyl]-phenol, 4-amino-2-methoxymethyl-phenol, 5-amino-2-hydroxy-benzoic acid, 1-(5-amino-2-hydroxy-phenyl)-ethane-1,2-diol, 4-amino-2-(2-hydroxy-ethyl)-phenol, 4-amino-3-(hydroxymethyl) phenol, 4-amino-3-fluoro-phenol, 4-amino-2-(aminomethyl)-phenol, and 4-amino-2-fluoro-phenol;

o-aminophenol derivatives such as: 2-amino-phenol (commonly known as o-aminophenol), 2,4-diaminophenol, 2-amino-5-methyl-phenol, 2-amino-6-methyl-phenol N-(4-amino-3-hydroxy-phenyl)-acetamide, and 2-amino4-methyl-phenol; and heterocyclic derivatives such as: pyrimidine-2,4,5,6-tetramine (commonly known as 2,4,5,6-tetraaminopyridine), 1-methyl-1H-pyrazole-4,5-diamine, 2-(4,5-diamino-1H-pyrazol-1-yl)ethanol,$N^2$,$N^2$-dimethyl-pyridine-2,5-diamine, 2-[(3-amino-6-methoxypyridin-2-yl)amino]ethanol, 6-methoxy-$N^2$-methyl-pyridine-2,3-diamine, 2,5,6-triaminopyrimidin-4(1H)-one, pyridine-2,5-diamine, 1-isopropyl-1H-pyrazole-4,5-diamine, 1-(4-methylbenzyl)-1H-pyrazole-4,5-diamine, 1-(benzyl)-1H-pyrazole-4,5-diamine, and 1-(4-chlorobenzyl)-1H-pyrazole-4,5-diamine.

The novel primary intermediates of formula (1) of this invention may be used with any suitable coupler(s) in hair coloring compositions or systems of this invention.

Suitable known couplers include, for example:

phenols, resorcinol and naphthol derivatives such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, 7-amino-4-hydroxy-naphthalene-2-sulfonic acid, 2-isopropyl-5-methylphenol, 1,2,3,4-tetrahydro-naphthalene-1,5-diol, 2-chloro-benzene-1,3-diol, 4-hydroxy-naphthalene-1-sulfonic acid, benzene-1,2,3-triol, naphthalene-2,3-diol, 5-dichloro-2-methylbenzene-1,3-diol, 4,6-dichlorobenzene-1,3-diol, and 2,3-dihydroxy-[1,4]naphthoquinone;

m-phenylenediamines such as: 2,4-diaminophenol, benzene-1,3-diamine, 2-(2,4-diamino-phenoxy)-ethanol, 2-[(3-amino-phenyl)-(2-hydroxy-ethyl)-amino]-ethanol, 2-mehyl-benzene-1,3-diamine, 2-[[2-(2,4-diamino-phenoxy)-ethyl]-(2-hydroxy-ethyl)-amino]-ethanol, 4-{3-[(2,4-diaminophenyl)oxy]propoxy}benzene-1,3-diamine, 2-(2,4-diamino-phenyl)-ethanol, 2-(3-amino-4-methoxy-phenylamino)-ethanol, 4-(2-amino-ethoxy)-benzene-1,3-diamine, (2,4-diamino-phenoxy)-acetic acid, 2-[2,4-diamino-5-(2-hydroxy-ethoxy)-phenoxy]-ethanol, 4-ethoxy-6-methyl-benzene-1,3-diamine, 2-(2,4-diamino-5-methyl-phenoxy)-ethanol, 4,6-dimethoxy-benzene-1,3-diamine, 2-[3-(2-hydroxy-ethylamino)-2-methyl-phenylamino]-ethanol, 3-(2,4-diamino-phenoxy)-propan-1-ol, N-[3-(dimethylamino)phenyl]urea, 4-methoxy-6-methylbenzene-1,3-diamine, 4-fluoro-6-methylbenzene-1,3-diamine, 2-({3-[(2-hydroxyethyl)amino]-4,6-dimethoxyphenyl}-amino)ethanol, 3-(2,4-diaminophenoxy)-propane-1,2-diol, 2-[2-amino-4-(methylamino)-phenoxy]ethanol, 2-[(5-amino-2-ethoxy-phenyl)-(2-hydroxy-ethyl)-amino]-ethanol, 2-[(3-aminophenyl)amino]ethanol, N-(2-aminoethyl)benzene-1,3-diamine, 4-{[(2,4-diamino-phenyl)oxy]methoxy}-benzene-1,3-diamine, and 2,4-dimethoxybenzene-1,3-diamine;

m-aminophenols such as: 3-amino-phenol, 2-(3-hydroxy4-methyl-phenylamino)-acetamide, 2-(3-hydroxy-phenylamino)-acetamide, 5-amino-2-methyl-phenol, 5-(2-hydroxy-ethylamino)-2-methyl-phenol, 5-amino-2,4-dichloro-phenol, 3-amino-2-methyl-phenol, 3-amino-2-chloro-6-methyl-phenol, 5-amino-2-(2-hydroxy-ethoxy)-phenol, 2-chloro-5-(2,2,2-trifluoro-ethylamino)-phenol, 5-amino4-chloro-2-methyl-phenol, 3-cyclopentylamino-phenol, 5-[(2-hydroxyethyl)amino]4-methoxy-2-methylphenol, 5-amino-4-methoxy-2-methylphenol, 3-(dimethylamino)phenol, 3-(diethylamino)phenol, 5-amino4-fluoro-2-methylphenol, 5-amino4-ethoxy-2-methylphenol, 3-amino-2,4-dichloro-phenol, 3-[(2-methoxyethyl)amino]phenol, 3-[(2-hydroxyethyl)amino]phenol, 5-amino-2-ethyl-phenol, 5-amino-2-methoxyphenol, 5-[(3-hydroxypropyl)amino]-2-methylphenol, 3-[(3-hydroxy-2-methylphenyl)-amino]propane-1,2-diol, and 3-[(2-hydroxyethyl)amino]-2-methylphenol; and heterocyclic derivatives such as: 3,4-dihydro-2H-1,4-benzoxazin-6-ol, 4-methyl-2-phenyl-2,4-dihydro-3H-pyrazol-3-one, 6-methoxyquinolin-8-amine, 4-methylpyridine-2,6-diol, 2,3-dihydro-1,4-benzodioxin-5-ol, 1,3-benzodioxol-5-ol, 2-(1,3-benzodioxol-5-ylamino)ethanol, 3,4-dimethylpyridine-2,6-diol, 5-chloropyridine-2,3-diol, 2,6-dimethoxypyridine-3,5-diamine, 1,3-benzodioxol-5-amine, 2-{[3,5-diamino-6-(2-hydroxy-ethoxy)-pyridin-2-yl]oxy}-ethanol, 1H-indol4-ol, 5-amino-2,6-dimethoxypyridin-3-ol, 1H-indole-5,6-diol, 1H-indol-7-ol, 1H-indol-5-ol, 1H-indol-6-ol, 6-bromo-1,3-benzodioxol-5-ol, 2-aminopyridin-3-ol, pyridine-2,6-diamine, 3-[(3,5-diaminopyridin-2-yl)oxy]propane-1,2-diol, 5-[(3,5-diaminopyridin-2-yl)oxy]pentane-1,3-diol, 1H-indole-2,3-dione, indoline-5,6-diol, 3,5-dimethoxypyridine-2,6-diamine, 6-methoxypyridine-2,3-diamine, and 3,4-dihydro-2H-1,4-benzoxazin-6-amine.

Preferred primary intermediates include:

p-phenylenediamine derivatives such as: 2-methyl-benzene-1,4-diamine, benzene-1,4-diamine, 1-(2,5-diamino-phenyl)-ethanol, 2-(2,5-diamino-phenyl)-ethanol, N-(2-methoxyethyl)benzene-1,4-diamine, 2-[(4-amino-phenyl)-(2-hydroxy-ethyl)-amino]-ethanol, and 1-(2,5-diaminophenyl)ethane-1,2-diol;

p-aminophenol derivatives such as 4-amino-phenol, 4-methylamino-phenol, 4-amino-3-methyl-phenol, 4-amino-2-methoxymethyl-phenol, and 1-(5-amino-2-hydroxy-phenyl)-ethane1,2-diol;

o-aminophenol derivatives such as: 2-amino-phenol, 2-amino-5-methyl-phenol, 2-amino-6-methyl-phenol, N-(4-amino-3-hydroxy-phenyl)-acetamide, and 2-amino-4-methyl-phenol; and heterocyclic derivatives such as: pyrimidine-2,4,5,6-tetramine, 1-methyl-1H-pyrazole-4,5-diamine, 2-(4,5-diamino-1H-pyrazol-1-yl)ethanol, 1-(4-methylbenzyl)-1H-pyrazole-4,5-diamine, 1-(benzyl)-1H-pyrazole-4,5-diamine, and $N^2$,$N^2$-dimethyl-pyridine-2,5-diamine.

Preferred couplers include:

phenols, resorcinol and naphthol derivatives such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, and 2-isopropyl-5-methylphenol;

m-phenylenediamines such as: benzene-1,3-diamine, 2-(2,4-diamino-phenoxy)-ethanol, 4-{3-[(2,4-diaminophenyl)oxy]propoxy}benzene-1,3-diamine, 2-(3-amino-4-methoxy-phenylamino)-ethanol, 2-[2,4-diamino-5-(2-hydroxy-ethoxy)-phenoxy]-ethanol, and 3-(2,4-diamino-phenoxy)-propan-1-ol;

m-aminophenols such as: 3-amino-phenol, 5-amino-2-methyl-phenol, 5-(2-hydroxy-ethylamino)-2-methyl-phenol, and 3-amino-2-methyl-phenol; and heterocyclic derivatives such as: 3,4-dihydro-2H-1,4-benzoxazin-6-ol, 4-methyl-2-phenyl-2,4-dihydro-3H-pyrazol-3-one, 1,3-benzodioxol-5-ol, 1,3-benzodioxol-5-amine, 1H-indol-4-ol, 1H-indole-5,6-diol, 1H-indol- 7-ol, 1H-indol-5-ol, 1H-indol-6-ol, 1H-indole-2,3-dione, pyridine-2,6-diamine, and 2-aminopyridin-3-ol.

Most preferred primary intermediates include:

p-phenylenediamine derivatives such as: 2-methyl-benzene-1,4-diamine, benzene-1,4-diamine, 2-(2,5-diamino-phenyl)-ethanol, 1-(2,5-diamino-phenyl)-ethanol, and 2-[(4-amino-phenyl)-(2-hydroxy-ethyl)-amino]-ethanol;

p-aminophenol derivatives such as: 4-amino-phenol, 4-methylamino-phenol, 4-amino-3-methyl-phenol, and 1-(5-amino-2-hydroxy-phenyl)-ethane-1,2-diol;

o-aminophenols such as: 2-amino-phenol, 2-amino-5-methyl-phenol, 2-amino-6-methyl-phenol, and N-(4-amino-3-hydroxy-phenyl)-acetamide; and heterocyclic derivatives such as: pyrimidine-2,4,5,6-tetramine, 2-(4,5-diamino-1H-pyrazol-1-yl)ethanol, 1-(4-methylbenzyl)-1H-pyrazole-4,5-diamine, and 1-(benzyl)-1H-pyrazole-4,5-diamine.

Most preferred couplers include:

phenols, resorcinol and naphthol derivatives such as: benzene-1,3-diol, 4-chlorobenzene-1,3-diol, naphthalen-1-ol, 2-methyl-naphthalen-1-ol, and 2-methyl-benzene-1,3-diol;

m-phenylenediamine such as: 2-(2,4-diamino-phenoxy)-ethanol, 2-(3-amino-4-methoxy-phenylamino)-ethanol, 2-[2,4-diamino-5-(2-hydroxy-ethoxy)-phenoxy]-ethanol, and 3-(2,4-diamino-phenoxy)-propan-1-ol;

m-aminophenols such as: 3-amino-phenol, 5-amino-2-methyl-phenol, 5-(2-hydroxy-ethylamino)-2-methyl-phenol, and 3-amino-2-methyl-phenol; and heterocyclic derivatives such as: 3,4-dihydro-2H-1,4-benzoxazin-6-ol, 4-methyl-2-phenyl-2,4-dihydro-3H-pyrazol-3-one, 1H-indol-6-ol, and 2-aminopyridin-3-ol.

Understandably, the coupler compounds and the primary intermediate compounds, including the novel compounds of the invention, in so far as they are bases, can be used as free bases or in the form of their physiologically compatible salts with organic or inorganic acids, such as hydrochloric, citric, acetic, tartaric, or sulfuric acids, or, in so far as they have aromatic OH groups, in the form of their salts with bases, such as alkali phenolates.

The total amount of dye precursors (e.g., primary intermediate and coupler compounds, including the novel compounds of this invention) in the hair dyeing compositions of this invention is generally from about 0.002 to about 20, preferably from about 0.04 to about 10, and most preferably from about 0.1 to about 7.0 weight percent, based on the total weight of the hair dyeing composition. The primary intermediate and coupler compounds are generally used in molar equivalent amounts. However, it is possible to use the primary intermediate compounds in either excess or deficiency, i.e., a molar ratio of primary intermediate to coupler generally ranging from about 5:1 to about 1:5.

The hair dyeing compositions of this invention will contain the primary intermediate of this invention in an effective dyeing amount, generally in an amount of from about 0.001 to about 10 weight percent by weight of the hair dye composition, preferably from about 0.01 to about 5.0 weight percent. Other primary intermediates, when present, are typically present in an amount such that in aggregate the concentration of primary intermediates in the composition is from about 0.002 to about 10 weight percent, preferably from about 0.01 to about 5.0 weight percent. The coupler(s) are present in an effective dyeing concentration, generally an amount of from about 0.001 to about 10.0 weight percent by weight of the hair dye composition, preferably from about 0.01 to about 5.0 weight percent. The remainder of the hair dye composition comprises a carrier or vehicle for the couplers and primary intermediates, and comprises various adjuvants as described below.

Any suitable carrier or vehicle, generally an aqueous or hydroalcoholic solution, can be employed, preferably an aqueous solution. The carrier or vehicle will generally comprise more than 80 weight percent of the hair dye composition, typically 90 to 99 weight percent, preferably 94 to 99 weight percent. The hair coloring compositions of this invention may contain as adjuvants one or more cationic, anionic, amphoteric, or zwitterionic surface active agents, perfumes, antioxidants such as ascorbic acid, thioglycolic acid or sodium sulfite, chelating and sequestering agents such as EDTA, thickening agents, alkalizing or acidifying agents, solvents, diluents, inerts, dispersing agents, penetrating agents, defoamers, enzymes, and other dye agents (e.g., synthetic direct and natural dyes). These adjuvants are cosmetic additive ingredients commonly used in compositions for coloring hair.

The hair dye compositions of the present invention are used by admixing them with a suitable oxidant, which reacts with the hair dye precursors to develop the hair dye. Any suitable oxidizing agent can be employed in the hair dye product compositions of this invention, particularly hydrogen peroxide ($H_2O_2$) or precursors therefor. Also suitable are urea peroxide, the alkali metal salts of persulfate, perborate, and percarbonate, especially the sodium salt, and melamine peroxide. The oxidant is usually provided in an aqueous composition generally referred to as the developer composition, which normally is provided as a separate component of the finished hair dye product and present in a separate container. The developer composition may also contain, to the extent compatible, various ingredients needed to form the developer composition, i.e., peroxide stabilizers, foam formers, etc., and may incorporate one or more of the adjuvants referred to above, e.g., surface active agents, thickeners, pH modifiers, etc. Upon mixing the hair coloring composition and the developer composition to form a hair dye product composition, the adjuvants are provided in the hair dye product composition as it is applied to the hair to achieve desired product attributes, e.g., pH, viscosity, rheology, etc.

The form of the hair dye product compositions according to the invention can be, for example, a solution, especially an aqueous or aqueous-alcoholic solution. However, the form that is preferred is a thick liquid, cream, gel or an emulsion whose composition is a mixture of the dye ingredients with the conventional cosmetic additive ingredients suitable for the particular preparation.

Suitable conventional cosmetic additive ingredients useful in the hair dye and developer compositions, and hence in the hair dye product compositions of this invention are described below, and may be used to obtain desired characteristics of the hair dye, developer, and hair dye product compositions.

Solvents: In addition to water, solvents that can be used are lower alkanols (e.g., ethanol, propanol, isopropanol, benzyl alcohol); polyols (e.g., carbitols, propylene glycol, hexylene glycol, glycerin). See WO 98/27941 (section on diluents) incorporated by reference. See also U.S. Pat. No. 6,027,538 incorporated by reference. Under suitable processing, higher alcohols, such as C8 to C18 fatty alcohols, especially cetyl alcohol, are suitable organic solvents, provided they are first liquified by melting, typically at low temperature (50 to 80° C.), before incorporation of other, usually lipophilic, materials.

The organic solvents are typically present in the hair dye compositions in an amount of from about 5 to about 30% by weight of the hair dye composition. Water is usually present in an amount of from about 5 to about 90% by weight of the hair dye composition, preferably from about 15 to about 75% by weight and most preferably from about 30 to about 65% by weight.

Surfactants: These materials are from the classes of anionic, cationic, amphoteric (including zwitterionic surfactants) or nonionic surfactant compounds. (Cationic surfactants, generally included as hair conditioning materials, are considered separately below.) Suitable surfactants, other than cationic surfactants, include fatty alcohol sulfates, ethoxylated fatty alcohol sulfates, alkylsulfonates, alkylbenzensulfonates, alkyltrimethylammonium salts, alkylbetaines, ethoxylated fatty alcohols, ethoxylated fatty acids, ethoxylated alkylphenols, block polymers of ethylene and/or propylene glycol, glycerol esters, phosphate esters, fatty acid alkanol amides and ethoxylated fatty acid esters, alkyl sulfates, ethoxylated alkyl sulfates, alkyl glyceryl ether sulfonates, methyl acyl taurates, acyl isethionates, alkyl ethoxy carboxylates, fatty acid mono- and diethanolamides. Especially useful are sodium and ammonium alkyl sulfates, sodium and ammonium ether sulfates having 1 to 3 ethylene oxide groups, and nonionic surfactants sold as Tergitols, e.g., C11–C15 Pareth-9, and Neodols, e.g., C12–C15 Pareth-3. They are included for various reasons, e.g., to assist in thickening, for forming emulsions, to help in wetting hair during application of the hair dye product composition, etc. Amphoteric surfactants include, for example, the asparagine derivatives as well betaines, sultaines, glycinates and propionates having an alkyl or alkylamido group of from about 10 to about 20 carbon atoms. Typical amphoteric surfactants suitable for use in this invention include lauryl betaine, lauroamphoglycinate, lauroamphopropionate, lauryl sultaine, myristamidopropyl betaine, myristyl betaine, stearoamphopropylsulfonate, cocamidoethyl betaine, cocamidopropyl betaine, cocoamphoglycinate, cocoamphocarboxypropionate, cocoamphocarboxyglycinate, cocobetaine, and cocoamphopropionate. Reference is made to WO 98/52523 published Nov. 26, 1998 and WO 01/62221 published Aug. 30, 2001, both incorporated herein by reference thereto.

The amount of surfactants in the hair dye compositions is normally from about 0.1% to 30% by weight, preferably 1% to 15% by weight.

Thickeners: Suitable thickeners include such as higher fatty alcohols, starches, cellulose derivatives, petrolatum, paraffin oil, fatty acids and anionic and nonionic polymeric thickeners based on polyacrylic and polyurethane polymers. Examples are hydroxyethyl cellulose, hydroxymethylcellulose and other cellulose derivatives, hydrophobically modified anionic polymers and nonionic polymers, particularly such polymers having both hydrophilic and hydrophobic moieties (i.e., amphiphilic polymers). Useful nonionic polymers include polyurethane derivatives such as PEG-150/stearyl alcohol/SDMI copolymer. Suitable polyether urethanes are Aculyn® 44 and Aculyn® 46 polymers sold by Rohm & Haas. Other useful amphiphilic polymers are disclosed in U.S. Pat. No. 6,010,541 incorporated by reference. See also WO 01/62221 mentioned above. Examples of anionic polymers that can be used as thickeners are acrylates copolymer, acrylates/ceteth-20 methacrylates copolymer, acrylates/ceteth-20 itaconate copolymer, and acrylates/beheneth-25 acrylates copolymers. In the case of the associative type of thickeners, e.g., Aculyns 22, 44 and 46, the polymer may be included in one of either the hair dye composition or the developer composition of the hair dye product and the surfactant material in the another. Thus, upon mixing of the hair dye and developer compositions, the requisite viscosity is obtained. The thickeners are provided in an amount to provide a suitably thick product as it is applied to the hair. Such products generally have a viscosity of from 1000 to 100000 cps, and often have a thixotropic rheology.

pH Modifying agents: Suitable materials that are used to adjust pH of the hair dye compositions include alkalizers such alkali metal and ammonium hydroxides and carbonates, especially sodium hydroxide and ammonium carbonate, ammonia, organic amines including methylethanolamine, aminomethylpropanol, mono-, di-, and triethanolamine, and acidulents such as inorganic and inorganic acids, for example phosphoric acid, acetic acid, ascorbic acid, citric acid or tartaric acid, hydrochloric acid, etc. See U.S. Pat. No. 6,027,538 incorporated by reference.

Conditioners: Suitable materials include silicones and silicone derivatives; hydrocarbon oils; monomeric quaternary compounds, and quaternized polymers. Monomeric quaternary compounds are typically cationic compounds, but may also include betaines and other amphoteric and zwitterionic materials that provide a conditioning effect. Suitable monomeric quaternary compounds include behentrialkonium chloride, behentrimonium chloride, benzalkonium bromide or chloride, benzyl triethyl ammonium chloride, bis-hydroxyethyl tallowmonium chloride, C12–18 dialkyldimonium chloride, cetalkonium chloride, ceteartrimonium bromide and chloride, cetrimonium bromide, chloride and methosulfate, cetylpyridonium chloride, cocamidoproypl ethyldimonium ethosulfate, cocamidopropyl ethosulfate, coco-ethyldimonium ethosulfate, cocotrimonium chloride and ethosulfate, dibehenyl dimonium chloride, dicetyldimonium chloride, dicocodimonium chloride, dilauryl dimonium chloride, disoydimonium chloride, ditallowdimonium chloride, hydrogenated tallow trimonium chloride, hydroxyethyl cetyl dimonium chloride, myristalkonium chloride, olealkonium chloride, soyethomonium ethosulfate, soytrimonium chloride, stearalkonium chloride, and many other compounds. See WO 98/27941 incorporated by reference. Quaternized polymers are typically cationic polymers, but may also include amphoteric and zwitterionic polymers. Useful polymers are exemplified by polyquaternium-4, polyquaternium-6, polyquaternium-7, polyquaternium-8, polyquaternium-9, polyquaternium-10, polyquaternium-22, polyquaternium-32, polyquaternium-39, polyquaternium-44 and polyquaternium-47. Silicones suitable to condition hair are dimethicone, amodimethicone, dimethicone copolyol and dimethiconol. See also WO 99/34770 published Jul. 15,1999, incorporated by reference, for suitable silicones. Suitable hydrocarbon oils would include mineral oil.

Conditioners are usually present in the hair dye composition in an amount of from about 0.01 to about 5% by weight of the hair dye composition.

Direct Dyes: The hair dyeing compositions according to the invention can also contain compatible direct dyes including Disperse Black 9, HC Yellow 2, HC Yellow 4, HC Yellow 15, 4-nitro-o-phenylenediamine, 2-amino-6-chloro-4-nitrophenol, HC Red 3, Disperse Violet 1, HC Blue 2, Disperse Blue 3, and Disperse Blue 377.

These direct dyes can be contained in the hair coloring compositions of the invention in an amount of from about 0.05 to 4.0 percent by weight.

Natural ingredients: For example, proteins and protein derivatives, and plant materials such as aloe, chamomile and henna extracts.

Other adjuvants include polysaccharides, alkylpolyglycosides, buffers, chelating and sequestrant agents, antioxidants, and peroxide stabilizing agents as mentioned in WO 01/62221, etc.

The adjuvants referred to above but not specifically identified that are suitable are listed in the International Cosmetics Ingredient Dictionary and Handbook, (Eighth Edition) published by The Cosmetics, Toiletry, and Fragrance Association, incorporated by reference. In particular reference is made to Volume 2, Section 3 (Chemical Classes) and Section 4 (Functions) are useful in identifying a specific adjuvant to achieve a particular purpose or multipurpose.

The above-mentioned conventional cosmetic ingredients are used in amounts suitable for their functional purposes. For example, the surfactants used as wetting agents, associative agents, and emulsifiers are generally present in concentrations of from about 0.1 to 30 percent by weight, the thickeners are useful in an amount of from about 0.1 to 25 percent by weight, and the hair care materials are typically used in concentrations of from about 0.01 to 5.0 percent by weight.

The hair dyeing product composition as it is applied to the hair, i.e., after mixing the hair dye composition according to the invention and the developer, can be weakly acidic, neutral or alkaline according to their composition. The hair dye compositions can have pH values of from about 6 to 11.5, preferably from about 6.8 to about 10, and especially from about 8 to about 10. The pH of the developer composition is typically acidic, and generally the pH is from about 2.5 to about 6.5, usually about 3 to 5. The pH of the hair dye and developer compositions is adjusted using a pH modifier as mentioned above.

In order to use the hair coloring composition for dyeing hair, the above-described hair coloring compositions according to the invention are mixed with an oxidizing agent immediately prior to use and a sufficient amount of the mixture is applied to the hair, according to the hair abundance, generally from about 60 to 200 grams. Some of the adjuvants listed above (e.g., thickeners, conditioners, etc.) can be provided in the dye composition or the developer, or both, depending on the nature of the ingredients, possible interactions, etc., as is well known in the art.

Typically, hydrogen peroxide, or its addition compounds with urea, melamine, sodium borate or sodium carbonate, can be used in the form of a 3 to 12 percent, preferably 6 percent, aqueous solution as the oxidizing agent for developing the hair dye. Oxygen can also be used as the oxidizing agent. If a 6 percent hydrogen peroxide solution is used as oxidizing agent, the weight ratio of hair coloring composition and developer composition is 5:1 to 1:5, but preferably 1:1. In general, the hair dyeing composition comprising primary intermediate(s) and coupler(s), including at least one of the compounds of formula (1), is prepared and then, at the time of use, the oxidizing agents, such as $H_2O_2$, contained in a developer composition is admixed therewith until an essentially homogenous composition is obtained, which is applied shortly after preparation to the hair to be dyed and permitted to remain in contact with the hair for a dyeing effective amount of time. The mixture of the oxidizing agent and the dye composition of the invention (i.e., the hair dye product composition) is allowed to act on the hair for about 2 to about 60 minutes, preferably about 15 to 45, especially about 30 minutes, at about 15 to 50° C., the hair is rinsed with water, and dried. If necessary, it is washed with a shampoo and rinsed, e.g., with water or a weakly acidic solution, such as a citric acid or tartaric acid solution. Subsequently the hair is dried. Optionally, a separate conditioning product may also be provided.

Together the hair dye composition of the present invention comprising the hair dye primary intermediate (1) and the developer composition comprising the oxidizing agent form a system for dyeing hair. This system may be provided as a kit comprising in a single package separate containers of the hair dye composition, the developer, the optional conditioner or other hair treatment product, and instructions for use.

Especially useful primary intermediates of formula (1) of this invention will provide hair coloring compositions having outstanding color fastness, especially light fastness, fastness to washing and fastness to rubbing.

DYEING EXAMPLE 1

The following composition shown in Table 1 can be used for dyeing Piedmont hair. 100 g of the dyeing composition is mixed with 100 g 20 volume hydrogen peroxide. The resulting mixture is applied to the hair and permitted to remain in contact with the hair for 30 minutes. The dyed hair is then shampooed, rinsed with water and dried. The ranges of ingredients set out in Table 1 are illustrative of useful concentrations of the recited materials in a hair dye product.

TABLE 1

Composition for Dyeing Hair

| Ingredients | Range (wt %) | Weight (%) |
|---|---|---|
| Cocamidopropyl betaine | 0–25 | 17.00 |
| Polyquaternium-22 | 0–7 | 5.00 |
| Monoethanolamine[1] | 0–15 | 2.00 |
| Oleic Acid | 2–22 | 0.75 |
| Citric Acid | 0–3 | 0.10 |
| 28% Ammonium hydroxide[1] | 0–15 | 5.00 |
| Behentrimonium chloride | 1–5 | 0.50 |
| Sodium sulfite | 0–1 | 0.10 |
| EDTA | 0–1 | 0.10 |
| Erythorbic acid | 0–1 | 0.40 |
| Ethoxydiglycol | 1–10 | 3.50 |
| C11–15 Pareth-9 (Tergitol 15-S-9) | 0.5–5 | 1.00 |
| C12–15 Pareth-3 (Neodol 25-3) | 0.25–5 | 0.50 |
| Isopropanol | 2–10 | 4.00 |
| Propylene glycol | 1–12 | 2.00 |
| p-phenylenediamine | 0–5 | 1 mmole |
| N,N-Bis(hydroxyethyl)-p-phenylene diamine | 0–5 | 1 mmole |
| 3-Methyl-p-aminophenol | 0–5 | 1 mmole |
| p-Aminophenol | 0–5 | 1 mmole |
| Primary Intermediate of this invention | 0.5–5 | 4 mmoles |
| 5-Amino-2-Methyl Phenol[2] | 0–5 | 3 mmoles |
| 2,4-Diaminophenoxyethanol[2] | 0–5 | 3 mmoles |
| M-Phenylenediamine[2] | 0–5 | 1 mmole |
| Water | qs to 100.00 | qs to 100.00 |

[1]In the aggregate, these ingredients are in the range of 2 to 15% by weight.
[2]At least one of these dye precursors is typically present.

Exemplary combinations of hair coloring components employing a 2-substituted-amino-5-methyl-phenol compound of formula (1) of this invention are shown in Table 1 and in combinations C1 to C116 in Tables A through G. Reading down the columns in Tables A through G, the Xes demonstrate combinations of dyes that can be formulated according to the present invention. For example, in Combination No. C1 in Column 4 of Table A, a primary intermediate compound of formula (1) of this invention (Row 1 of Table A), where R is defined before, can be combined with 2-amino-phenol. Especially preferred as the primary intermediate compounds of formula (1) in such combinations of Table 1 and Tables A through G are the following:

2-benzylamino-5-methyl-phenol;

5-methyl-2-[1-H-pyrrol-2-ylmethyl)-amino]-phenol;

2-isopropylamino-5-methyl-phenol; and 5-methyl-2-[(thiophen-2-ylmethyl)-amino]-phenol.

TABLE A

Dye Combinations

| Structure | IUPAC Name | Name | C1 | C2 | C3 | C4 | C5 | C6 | C7 | C8 | C9 | C10 | C11 |
|---|---|---|---|---|---|---|---|---|---|---|---|---|---|
| (2-amino-4-methylphenol with NHR) | 2-Methyl-benzene-1,4-diamine | p-Toluene-diamine | x | x | x | x | x | x | x | x | x | x | x |
| (benzene-1,4-diamine) | Benzene-1,4-diamine | p-Phenylene-diamine | | | | | | | | | | | |
| (N,N-bis(2-hydroxyethyl)-p-phenylenediamine) | 2-[(4-Amino-phenyl)-(2-hydroxy-ethyl)-amino]-ethanol | N,N-Bis(2-hydroxyethyl)-p-phenylene-diamine | | | | | | | | x | | | |
| (4-aminophenol) | 4-Amino-phenol | p-Aminophenol | | | | | | | | | x | | |
| (4-amino-3-methylphenol) | 4-Amino-3-methyl-phenol | 3-Methyl-p-aminophenol | | | | | | | | | | | |
| (2-aminophenol) | 2-Amino-phenol | o-Aminophenol | | | | | | | | | | x | |
| (benzene-1,3-diol) | Benzene-1,3-diol | Resorcinol | | x | | | | | | | | | x |

TABLE A-continued

Dye Combinations

| Structure | IUPAC Name | Name | C1 | C2 | C3 | C4 | C5 | C6 | C7 | C8 | C9 | C10 | C11 |
|---|---|---|---|---|---|---|---|---|---|---|---|---|---|
| 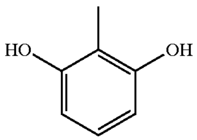 | 2-Methyl-benzene-1,3-diol | 2-Methyl-resorcinol | | | x | | | | | | | | |
| 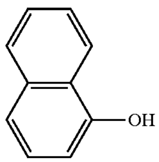 | Naphthalen-1-ol | 1-Naphthol | | | | | x | | | | | | |
| 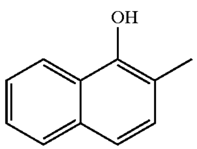 | 2-Methyl-naphthalen-1-ol | 2-Methyl-1-naphthol | | | | | | x | | | | | |
| 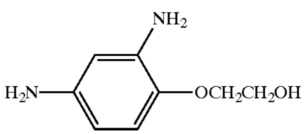 | 2-(2,4-Diaminophenoxy)-ethanol | 2,4-Diamino-phenoxyethanol | | | | | | | x | | | | |
| 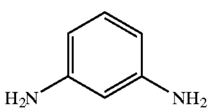 | Benzene-1,3-diamine | m-Phenylenediamine | | | | | | | | | x | | |
| 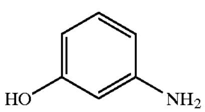 | 3-Amino-phenol | m-Aminophenol | | | | | | | | | | x | |

TABLE A-continued

Dye Combinations

| Structure | IUPAC Name | Name | C1 | C2 | C3 | C4 | C5 | C6 | C7 | C8 | C9 | C10 | C11 |
|---|---|---|---|---|---|---|---|---|---|---|---|---|---|
| ![structure] | 5-Amino-2-methyl-phenol | 2-Hydroxy-4-aminotoluene | | | | | | | | | | x | |
| ![structure] | 2-(4,5-Diamino-pyrazol-1-yl)-ethanol | 1-Hydroxyethyl-4,5-diamino-pyrazole | | | | | | | | | | | |

TABLE B

Dye Combinations

| Structure | C12 | C13 | C14 | C15 | C16 | C17 | C18 | C19 | C20 | C21 | C22 | C23 | C24 | C25 | C26 | C27 | C28 | C29 |
|---|---|---|---|---|---|---|---|---|---|---|---|---|---|---|---|---|---|---|
| 2-(R-amino)-4-methylphenol (OH, NHR) | x | x | x | x | x | x | x | x | x | x | x | x | x | x | x | x | x | x |
| 2,5-diaminotoluene (NH₂, NH₂) | | x | x | x | x | x | x | | | | | | | | | | | |
| p-phenylenediamine (NH₂, NH₂) | | | x | x | x | x | | | | | | | | | | | | |
| N,N-bis(2-hydroxyethyl)-p-phenylenediamine | x | | | | | | x | | | | | | | | | | | |
| p-aminophenol (NH₂, OH) | | | | | | | | x | x | x | x | x | x | x | x | x | | |
| 4-amino-m-cresol (NH₂, OH, CH₃) | | | | | | | | x | | | | | | | | | | |
| 2-aminophenol (OH, NH₂) | | | | | | | | | x | | | | | | | | x | x |
| resorcinol (OH, OH) | | | | | | | | | | | | | | | | | | x |

TABLE B-continued

| Structure | Dye Combinations | | | | | | | | | | | | | | | | | |
|---|---|---|---|---|---|---|---|---|---|---|---|---|---|---|---|---|---|---|
| | C12 | C13 | C14 | C15 | C16 | C17 | C18 | C19 | C20 | C21 | C22 | C23 | C24 | C25 | C26 | C27 | C28 | C29 |
| 2-methylresorcinol | x | | | | | | | | | | | | | | | | | |
| 1-naphthol | | x | | | | | | | | x | | | | | | | | |
| 2-methyl-1-naphthol | | | x | | | | | | | | x | | | | | | | x |
| 2-amino-4-aminophenol OCH₂CH₂OH ether | | | | x | | | | | | | | x | | | | | x | |
| m-phenylenediamine | | | | | x | | | | | | | | x | x | | | | |
| 3-aminophenol | | | | | | x | | | | | | | | | x | | | |

TABLE B-continued

| Structure | Dye Combinations | | | | | | | | | | | | | | | | | |
|---|---|---|---|---|---|---|---|---|---|---|---|---|---|---|---|---|---|---|
| | C12 | C13 | C14 | C15 | C16 | C17 | C18 | C19 | C20 | C21 | C22 | C23 | C24 | C25 | C26 | C27 | C28 | C29 |
| 5-amino-2-methylphenol (H₂N–C₆H₃(CH₃)–OH) | | | | | | | x | | | | | | | | | | | |
| 4,5-diamino-1-(2-hydroxyethyl)pyrazole | | | | | | | | | | | | | | | | x | | |

TABLE C

| Structure | Dye Combinations | | | | | | | | | | | | | | | | | |
|---|---|---|---|---|---|---|---|---|---|---|---|---|---|---|---|---|---|---|
| | C30 | C31 | C32 | C33 | C34 | C35 | C36 | C37 | C38 | C39 | C40 | C41 | C42 | C43 | C44 | C45 | C46 | C47 |
| 2-(R-amino)-5-methylphenol (OH, NHR, CH₃) | x | x | x | x | x | x | x | x | x | x | x | x | x | x | x | x | x | x |
| 2-methyl-1,4-phenylenediamine | | | | | | x | x | x | x | x | x | x | x | x | x | x | x | x |
| 1,4-phenylenediamine | | | | | | | x | x | x | x | x | x | | x | x | x | x | x |
| N,N-bis(2-hydroxyethyl)-p-phenylenediamine | | | | | | | | | | | | x | x | | | | | |
| 4-aminophenol | | | | | | | | | | | | | | x | | | | |
| 3-methyl-4-aminophenol | | | | | | x | | | | | | | | | | | | |
| 2-aminophenol | x | x | x | x | x | x | x | x | x | x | x | x | x | x | x | x | x | x |
| 1,3-dihydroxybenzene (resorcinol) | x | | | | | | | | | | | x | | x | x | x | x | x |

TABLE C-continued
Dye Combinations
| Structure | C30 | C31 | C32 | C33 | C34 | C35 | C36 | C37 | C38 | C39 | C40 | C41 | C42 | C43 | C44 | C45 | C46 | C47 |
|---|---|---|---|---|---|---|---|---|---|---|---|---|---|---|---|---|---|---|
| 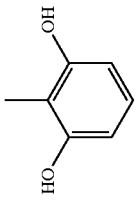 | | | | | | | x | | | | | | | | | | | |
| 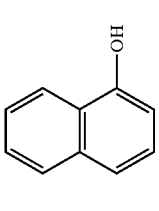 | x | | | | | | | x | | | | | | | | | | |
| 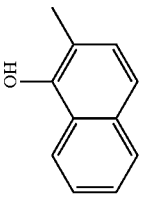 | | x | | | | | | | x | | | | | | x | | | |
| 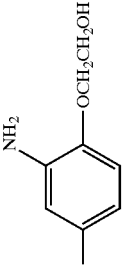 | | | x | | | | | | | x | | | | | | x | | |
| 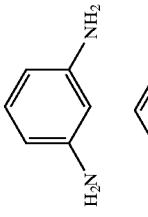 | | | | x | | | | | | | x | | | | | | x | |
| 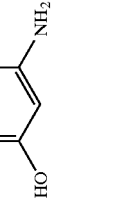 | | | | | | | | | | | | x | | | | | | x |

TABLE C-continued

| Structure | Dye Combinations | | | | | | | | | | | | | | | | | |
|---|---|---|---|---|---|---|---|---|---|---|---|---|---|---|---|---|---|---|
| | C30 | C31 | C32 | C33 | C34 | C35 | C36 | C37 | C38 | C39 | C40 | C41 | C42 | C43 | C44 | C45 | C46 | C47 |
| 5-amino-2-methylphenol (H2N–C6H3(CH3)–OH) | | | | | x | | | | | | | | | | | | | |
| 4,5-diamino-1-(2-hydroxyethyl)pyrazole | | | | | | | | | | | | | x | | | | | |

TABLE D

| Structure | Dye Combinations | | | | | | | | | | | | | | | | | |
|---|---|---|---|---|---|---|---|---|---|---|---|---|---|---|---|---|---|---|
| | C48 | C49 | C50 | C51 | C52 | C53 | C54 | C55 | C56 | C57 | C58 | C59 | C60 | C61 | C62 | C63 | C64 | C65 |
| 2-(NHR)-4-methylphenol (OH, NH-R) | x | x | x | x | x | x | x | x | x | x | x | x | x | x | x | x | x | x |
| 2,5-diaminotoluene (NH$_2$, NH$_2$, CH$_3$) | | x | x | | | | | | | | | | | | | | | |
| 1,4-phenylenediamine (NH$_2$, NH$_2$) | x | | | | | | | | | | | | | | | | | |
| N,N-bis(2-hydroxyethyl)-p-phenylenediamine | | | | | | | | | | | | | | | | | | |
| 4-aminophenol (NH$_2$, OH) | | | | x | x | x | x | x | x | x | x | | | | | | | |
| 4-amino-3-methylphenol (NH$_2$, CH$_3$, OH) | | | | x | | | | | | | | x | | | | | | |
| 2-aminophenol (OH, NH$_2$) | x | x | x | x | x | x | x | x | x | x | x | x | x | x | x | x | x | x |
| 1,3-dihydroxybenzene (OH, OH) | | | | | | | | | | | | | x | x | x | x | x | x |

TABLE D-continued

| Structure | Dye Combinations | | | | | | | | | | | | | | | | | |
|---|---|---|---|---|---|---|---|---|---|---|---|---|---|---|---|---|---|---|
| | C48 | C49 | C50 | C51 | C52 | C53 | C54 | C55 | C56 | C57 | C58 | C59 | C60 | C61 | C62 | C63 | C64 | C65 |
| 2-methylresorcinol | | | | | x | | | | | | | | x | | | | | |
| 1-naphthol | | | | | | x | | | | | | | | x | | | | |
| 2-methyl-1-naphthol | | | | | | | x | | | | | | | | x | | | |
| 4-amino-2-(2-hydroxyethoxy)aniline | | | | | | | | x | | | | | | | | x | | |
| m-phenylenediamine | x | | | | | | | | x | | | | | | | | x | |
| 3-aminophenol | | x | | | | | | | | x | | | | | | | | x |

TABLE D-continued

Dye Combinations

| Structure | C48 | C49 | C50 | C51 | C52 | C53 | C54 | C55 | C56 | C57 | C58 | C59 | C60 | C61 | C62 | C63 | C64 | C65 |
|---|---|---|---|---|---|---|---|---|---|---|---|---|---|---|---|---|---|---|
| 5-amino-2-methylphenol (H₂N–C₆H₃(CH₃)–OH) | | | x | | | | | | | | | | | | | | | |
| 4,5-diamino-1-(2-hydroxyethyl)pyrazole | | | | | | | | | | | x | | | | | | | |

TABLE E

Dye Combinations

| Structure | C66 | C67 | C68 | C69 | C70 | C71 | C72 | C73 | C74 | C75 | C76 | C77 | C78 | C79 | C80 | C81 | C82 | C83 |
|---|---|---|---|---|---|---|---|---|---|---|---|---|---|---|---|---|---|---|
| 2-amino-4-methylphenol (OH, NH-R) | x | x | x | x | x | x | x | x | x | x | x | x | x | x | x | x | x | x |
| 2-methyl-p-phenylenediamine | | x | | | | | | | | | | | | | | | | |
| p-phenylenediamine | | | | | | | | | | | | | | | | | | |
| N,N-bis(2-hydroxyethyl)-p-phenylenediamine | | | | | x | x | x | x | | | | | | | | | | |
| 4-aminophenol | | | | | | | | | | x | x | x | x | x | x | x | x | x |
| 4-amino-3-methylphenol | | | | | | | | | | x | | | | | | | | |
| 2-aminophenol | x | x | | | | | | | | | x | | | | | | | |
| resorcinol | x | | | | | | | | | | | | | | | | | |

TABLE E-continued

Dye Combinations

| Structure | C66 | C67 | C68 | C69 | C70 | C71 | C72 | C73 | C74 | C75 | C76 | C77 | C78 | C79 | C80 | C81 | C82 | C83 |
|---|---|---|---|---|---|---|---|---|---|---|---|---|---|---|---|---|---|---|
| 2-methylbenzene-1,3-diol (OH, CH3, OH) | | | x | | | | | | | | | | | | | | | |
| naphthalen-1-ol | | | | x | | | | | | | | x | | | | | | |
| 2-methylnaphthalen-1-ol | | | | | x | | | | | | | | x | | | | | |
| 2-amino-4-(2-hydroxyethoxy)aniline | | | | | | x | | | | | | | | x | | | | |
| benzene-1,3-diamine | | | | | | | x | | | | | | | | x | | | |
| 3-aminophenol | | | | | | | | x | | | | | | | | x | x | |

TABLE E-continued

Dye Combinations

| Structure | C66 | C67 | C68 | C69 | C70 | C71 | C72 | C73 | C74 | C75 | C76 | C77 | C78 | C79 | C80 | C81 | C82 | C83 |
|---|---|---|---|---|---|---|---|---|---|---|---|---|---|---|---|---|---|---|
| 5-amino-2-methylphenol (H₂N–C₆H₃(CH₃)–OH) | x | | | | | | | | | | | | | | | | | |
| 4,5-diamino-1-(2-hydroxyethyl)pyrazole | | | | | | | | | x | x | x | x | x | x | x | x | x | x |

TABLE F

Dye Combinations

| Structure | C84 | C85 | C86 | C87 | C88 | C89 | C90 | C91 | C92 | C93 | C94 | C95 | C96 | C97 | C98 | C99 | C100 | C101 |
|---|---|---|---|---|---|---|---|---|---|---|---|---|---|---|---|---|---|---|
| 2-amino-5-methylphenol (NHR) | x | x | x | x | x | x | x | x | x | x | x | x | x | x | x | x | x | x |
| 2,5-diaminotoluene | | x | x | x | x | x | x | x | x | x | x | x | x | x | x | x | x | |
| p-phenylenediamine | | | | | | | | | | x | x | x | x | x | x | x | | |
| N,N-bis(2-hydroxyethyl)-p-phenylenediamine | x | | | | | | | | | | | | | | | | | x |
| p-aminophenol | | | | | | | | | x | | | | | | | | | |
| 2-methyl-4-aminophenol | | | x | x | x | x | x | x | | | | | | | | | | |
| 2-aminophenol | | x | | | | | | | | x | | | | | | | | |
| resorcinol | | | | | | | | | | | | | | | | | x | x |

TABLE F-continued
Dye Combinations
| Structure | C84 | C85 | C86 | C87 | C88 | C89 | C90 | C91 | C92 | C93 | C94 | C95 | C96 | C97 | C98 | C99 | C100 | C101 |
|---|---|---|---|---|---|---|---|---|---|---|---|---|---|---|---|---|---|---|
|  |  |  | x |  |  |  |  |  |  |  |  |  |  |  |  |  |  |  |
|  |  |  |  | x |  |  |  |  |  |  | x |  |  |  |  |  |  |  |
|  |  |  |  |  | x |  |  |  |  |  |  | x |  |  |  |  |  |  |
|  |  |  |  |  |  |  | x |  |  |  |  |  |  |  | x |  |  |  |
|  |  |  |  |  |  |  | x |  |  |  |  |  |  |  | x |  |  |  |
|  |  |  |  |  |  |  |  | x |  |  |  |  |  |  |  | x |  |  |

TABLE F-continued

Dye Combinations

| Structure | C84 | C85 | C86 | C87 | C88 | C89 | C90 | C91 | C92 | C93 | C94 | C95 | C96 | C97 | C98 | C99 | C100 | C101 |
|---|---|---|---|---|---|---|---|---|---|---|---|---|---|---|---|---|---|---|
| 5-amino-2-methylphenol (H₂N–C₆H₃(CH₃)–OH) | | | | | | | | | x | | | | | | | | x | |
| 4,5-diamino-1-(2-hydroxyethyl)pyrazole | x | x | x | x | x | x | x | x | x | x | x | x | x | x | x | x | x | x |

TABLE G

| Structure | Dye Combinations | | | | | | | | | | | | | | |
|---|---|---|---|---|---|---|---|---|---|---|---|---|---|---|---|
| | C102 | C103 | C104 | C105 | C106 | C107 | C108 | C09 | C110 | C111 | C112 | C113 | C114 | C115 | C116 |
| 2-amino-4-methylphenol (OH, CH3, NHR) | x | x | x | x | x | x | x | x | x | x | x | x | x | x | x |
| 2-methyl-1,4-phenylenediamine | | | | | | | | | | | | | | | |
| 1,4-phenylenediamine | x | x | x | x | x | x | x | | | | | | | | |
| N,N-bis(2-hydroxyethyl)-p-phenylenediamine | | | | | | | | | | | | | | | |
| 4-aminophenol | | | | | | | | | | | | | | | |
| 4-amino-3-methylphenol | | | | | | | | | | | | | | | |
| 2-aminophenol | | | | | | | | | | | | | | | |
| resorcinol | | | | | | | | | x | | | | | | |
| 2-methylresorcinol | | x | | | | | | | | x | | | | | |
| 1-naphthol | | | x | | | | | | | | x | | | | |
| 2-methyl-1-naphthol | | | | x | | | | | | | | x | | | |

TABLE G-continued

| | Dye Combinations | | | | | | | | | | | | | | |
|---|---|---|---|---|---|---|---|---|---|---|---|---|---|---|---|
| Structure | C102 | C103 | C104 | C105 | C106 | C107 | C108 | C09 | C110 | C111 | C112 | C113 | C114 | C115 | C116 |
| 2-amino-4-aminophenyl-OCH₂CH₂OH | | | x | | | | | | | | | x | | | |
| 1,3-diaminobenzene | | | | x | | | | | | | | | x | | |
| 3-aminophenol | | | | | x | | | | | | | | | x | |
| 5-amino-2-methylphenol | | | | | | x | | | | | | | | | x |
| 4,5-diamino-1-(2-hydroxyethyl)pyrazole | x | x | x | x | x | x | x | x | x | x | x | x | x | x | x |

With the foregoing description of the invention, those skilled in the art will appreciate that modifications may be made to the invention without departing from the spirit thereof. Therefore, it is not intended that the scope of the invention be limited to the specific embodiments illustrated and described.

We claim:

1. A compound of formula (1):

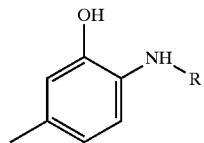

(1)

wherein R is selected from the group consisting of $C_1$ to $C_5$ hydroxyalkyl, a $C_3$ to $C_6$ cyclic ring containing hetero atoms selected from O, S and N atoms, and —$CH_2$—Ar where Ar is an aromatic ring wherein the aromatic ring may be substituted with one or two hydroxy, $C_1$ to $C_3$ alkoxy, or amino groups.

2. A compound of claim 1 wherein R is selected from the group consisting of benzyl, thiophen-ylmethyl, and pyrrolylmethyl.

3. A compound of claim 2 wherein R is benzyl.

4. A compound of claim 2 wherein R is thiophen-ylmethyl.

5. A compound of claim 3 wherein R is pyrrolylmethyl.

\* \* \* \* \*